United States Patent [19]

Kinoshita

[11] 4,361,138
[45] Nov. 30, 1982

[54] VENTILATION/FEEDWATER SWITCHING APPARATUS FOR ENDOSCOPE

[75] Inventor: Kunio Kinoshita, Hachioji, Japan

[73] Assignee: Olympus Optical Company Ltd., Japan

[21] Appl. No.: 216,943

[22] Filed: Dec. 16, 1980

[30] Foreign Application Priority Data

Mar. 31, 1980 [JP] Japan .......................... 55-42592[U]
Apr. 8, 1980 [JP] Japan ............................ 55-46107

[51] Int. Cl.³ .............................................. A61B 1/12
[52] U.S. Cl. ........................................ 128/4; 128/247
[58] Field of Search ........................................ 128/4-8, 128/240, 247, 274

[56] References Cited

U.S. PATENT DOCUMENTS

| | | | |
|---|---|---|---|
| 3,517,669 | 6/1970 | Buono et al. | 128/276 |
| 3,674,010 | 7/1972 | Falenks | 128/4 X |
| 3,726,272 | 4/1973 | Fukami et al. | 128/6 |
| 3,791,379 | 2/1974 | Storz | 128/4 |
| 3,903,877 | 9/1975 | Terada | 128/6 |
| 3,958,566 | 5/1976 | Furihata | 128/4 |
| 4,261,343 | 4/1981 | Ouchi et al. | 128/4 |
| 4,281,646 | 8/1981 | Kinoshita | 128/6 |

FOREIGN PATENT DOCUMENTS 48-10706 3/1973 Japan ...................................... 128/6

Primary Examiner—Lee S. Cohen
Assistant Examiner—Angela D. Sykes
Attorney, Agent, or Firm—Ostrolenk, Faber, Gerb & Soffen

[57] ABSTRACT

A ventilation and feedwater switching apparatus for an endoscope including a tubular member adapted to be fixedly mounted in an operating end of an endoscope, and adapted to have a ventilation tube and a feedwater tube connected to it, in such a manner that the tubular body is disposed in a ventilation path and a feedwater path. A cylindrical sliding valve body is slidably and removably fitted in the tubular body to permit switching between the ventilation and the water feed operation. The sliding valve body has an air discharge port at its upper end, and at its lower end an air delivery port which is normally closed by a check valve body which is detachably mounted thereon. In one preferred embodiment, a valve push rod is disposed in and extends through the sliding valve body, and forces the check valve body open in response to an external push.

6 Claims, 5 Drawing Figures

VENTILATION/FEEDWATER SWITCHING APPARATUS FOR ENDOSCOPE

BACKGROUND OF THE INVENTION

The invention relates to a ventilation/feedwater switching apparatus for an endoscope, and more particularly, to such switching apparatus used in a medical endoscope which is adapted to be inserted into a coeliac cavity and which includes a bottomed tubular body disposed in a ventilation/feedwater path and a sliding valve body which is slidably fitted in the tubular body to perform switching between the ventilation and the feedwater that is supplied to the distal end of the endoscope.

As is well recognized, an endoscope is adapted to be connected to a water feeder which supplies water to clean an observation window disposed in the distal end of a portion of the endoscope which is inserted into a coeliac cavity, or to a ventilator which supplies air into the distal end to cause an inflation of the coeliac cavity to facilitate an observation. Accordingly, the endoscope is associated with a ventilation/feedwater switching apparatus to control the supply of either water or air from such units to the distal end of the endoscope.

FIG. 1 illustrates essential parts of a typical endoscope which is associated with such a ventilation/feedwater switching apparatus. Endoscope 1 includes a proximate operating end 2 located outside a coeliac cavity to permit a variety of operations to be achieved, a portion 3 contiguous with the operating end 2 and which is adapted to be inserted into a coeliac cavity, a distal end 4 located in contiguous relationship with the outer or distal end of the portion 3, an eyepiece assembly 5 projecting from the operating end 2, and a connecting tube 6 which connects the endoscope 1 with a ventilator (not shown) and a water feeder (not shown). A ventilation path and a feedwater path are defined by a ventilation tube 7 and a feedwater tube 8, respectively, which extend through the connection tube 6 and the portion 3 successively. A ventilation/feedwater switching apparatus 9 is disposed within the proximate operating end 2 and connected with the tubes 7, 8. It will be noted that the both tubes 7, 8 are joined together adjacent to the outer or distal end of the portion 3 and are connected with an injection nozzle 10 which is disposed in the distal end 4.

FIG. 2 shows an exemplary construction of a conventional ventilation/feedwater switching apparatus 9. As shown, it comprises a bottomed tubular body 11 to which the ventilation tube 7 and the feedwater tube 8 are connected, a cylindrical sliding valve body 12 which is slidably fitted in the tubular body 11, a check valve body 13 of a resilient material and having one end fixedly connected to the tubular body 11 so as to open or close a valve opening 16 which is formed in a partition located toward the lower end of the tubular body 11, a coiled compression spring 14 urging the valve body 12 in a direction to project out of the tubular body 11, and a plurality of O rings 15 interposed between the tubular body 11 and the sliding valve body 12 to prevent water leakage.

It will be noted that around part of the outer peripheral surface, the sliding valve body 12 is formed with an elongate groove 12b which is engaged by a pin 11a projecting inwardly from the tubular body 11 to control the vertical position of the valve body 12.

Under its normal condition when the switching apparatus 9 is not operated, the resilience of the spring 14 urges the sliding valve body 12 upward, thereby closing the feedwater tube 8 and allowing the ventilation tube 7 to communicate with the tubular body 11 to permit flow of air from the ventilator into the tubular body 11. When an air discharge port 12a which represents the upper opening of a bore 12c formed in the sliding valve body 12 is open, the flow resistance of a channel extending through the discharge port 12a is less than the flow resistance of a channel extending through the check valve 13 and ventilation tube 7 to the distal end 4 of the endoscope 1, so that upon entering the tubular body 11, the air will find its way through the bore 12c to be discharged externally through the air discharge port 12a.

However, when the port 12a is blocked by a finger 17 as indicated in FIG. 2, the interruption of the air flow to the exterior through the port 12a causes an increase in the internal pressure within the tubular body 11. Thereupon, this air pressure acts on the check valve body 13 to cause it to be folded back around a thinner portion 13a thereof, thus opening the valve opening 16 to feed the air into the distal end 4 of the endoscope 1 through the ventilation tube 7.

When the sliding valve body 12 is pushed into the tubular body 11 while closing the air discharge port 12a with the finger 17, the valve body 12 then blocks the ventilation tube 7 on its inlet side, and a circumferentially extending groove 18 formed in the outer peripheral surface of the sliding valve body 12 moves into communication with the feedwater tube 8 on its inlet side, whereby the water from the water feeder is fed into the distal end 4 of the endoscope 1.

When the sliding valve body 12 is released, the resilience of the spring 14 returns the valve body to its upper position, whereby the inlet side of the feedwater tube 8 is blocked again while the inlet side of the ventilation tube 7 becomes open, allowing the air to be discharged through the port 12a. The ventilation/feedwater switching apparatus 9 now returns to its inoperative condition.

With the conventional apparatus 9 mentioned above, there is experienced the inconvenience that a fluid within the coeliac cavity, such as blood or another contaminant, may flow backward through the ventilation tube 7 to the operating end 2 where it may cause the check valve body 13 to be fixed or to stick by coagulation. Also, when the endoscope 1 is left out of service for a prolonged period of time, the valve body 13 may be held tightly around the valve opening 16, causing a failure to open the ventilation path. In the event of such occurrence, a remedy is effected with the described switching apparatus 9 by inserting a push rod 19 of a reduced diameter through the air discharge port 12a of the sliding valve body 12 so that the free end of the rod 19 may be driven against the valve body 13 to separate it from around the valve opening 16.

While this remedy removes the valve body 13 from sticking or adhesion with the valve opening 16, it is possible that the valve body 13 itself may be broken. In such instance, replacement or repair thereof is very troublesome. Specifically, since the valve body 13 is fixedly connected to the tubular body 11 toward its lower end, a troublesome operation is required in that the proximate operating end 2 must be disassembled and the tubular body 11 and ventilation tube 7 must be removed before the valve body 13 can be changed.

SUMMARY OF THE INVENTION

It is an object of the invention to provide a ventilation/feedwater switching apparatus for an endoscope in which a sliding valve body is fitted in a bottomed tubular body in a detachable manner and a check valve body is detachably mounted on an air delivery port of the sliding valve body.

It is another object of the invention to provide a ventilation/feedwater switching apparatus for an endoscope in which a valve pushing rod is assembled into a sliding valve body.

In accordance with the invention, whenever a check valve body is broken or otherwise damaged, the check valve body can be simply dismounted from within the tubular body together with the sliding valve body, thus facilitating the replacement and repair of the check valve body.

When the check valve body sticks, the simple manual operation of driving a valve pushing rod into the sliding valve body easily frees the check valve body, without requiring the separate provision of a push rod of a reduced diameter. In this manner, there is provided a ventilation/feedwater switching apparatus which has a high practical utility.

DESCRIPTION OF PREFERRED EMBODIMENTS

Figure 1:
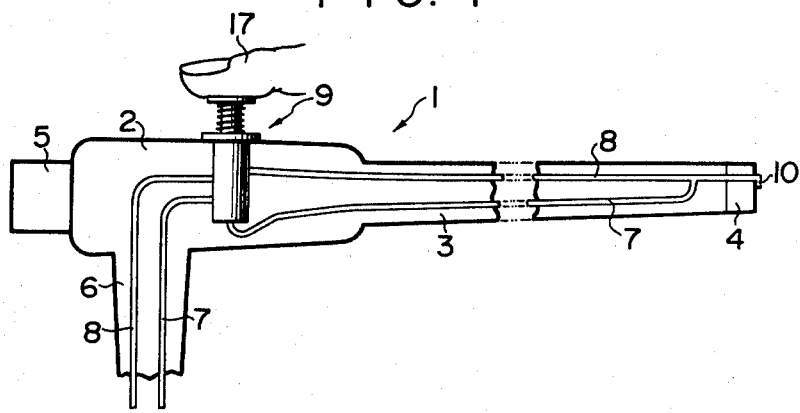
FIG. 1 is a schematic view of essential parts of an endoscope in which a conventional ventilation/feedwater switching apparatus is disposed.
Figure 2:
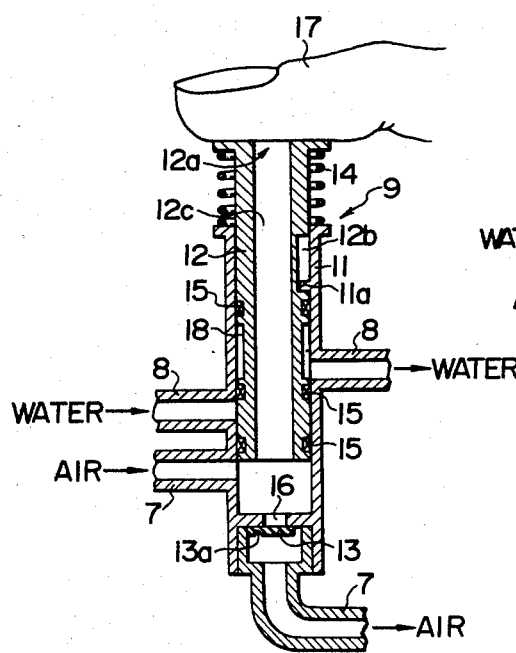
FIG. 2 is a longitudinal section of an exemplary ventilation/feedwater switching apparatus of the prior art.
Figure 3:
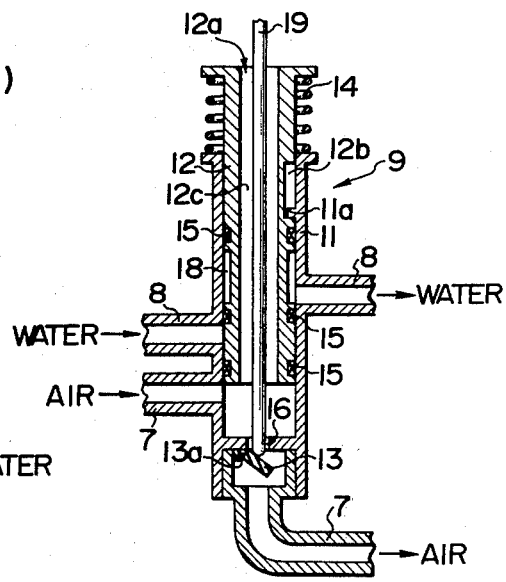
FIG. 3 is a longitudinal section of the ventilation/feedwater switching apparatus of FIG. 2, illustrating the remedy which is used when the check valve body sticks to the sliding valve body.
Figure 4:
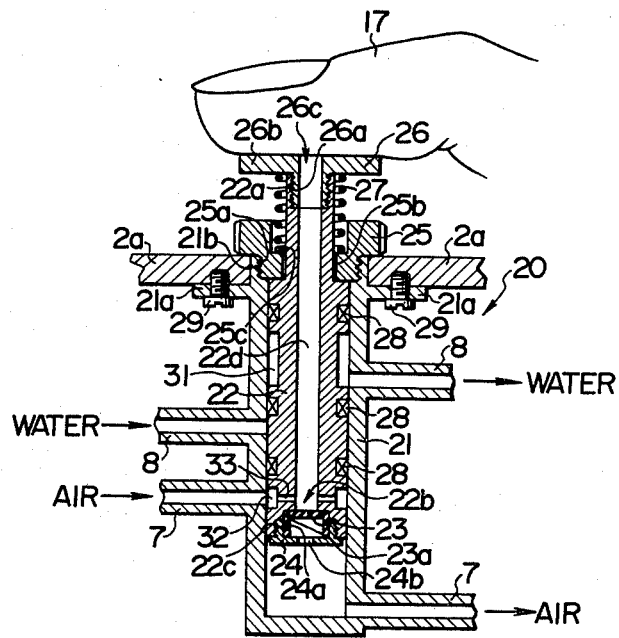
FIG. 4 is a longitudinal section of a ventilation/feedwater switching apparatus for endoscope according to one embodiment of the invention.

Referring to FIG. 4, there is shown a ventilation/feedwater switching apparatus 20 according to the invention. It comprises a bottomed tubular body 21 to which a ventilation tube 7 and a feedwater tube 8 are connected, a cylindrical sliding valve body 22 which is slidably fitted within the tubular body 21 in a water and air tight manner, a check valve body 23 formed of a resilient material such as rubber, plastic or the like and which is detachably mounted over an air delivery port 22b formed in the lower end of the sliding valve body 22, a check valve body retainer 24 for retaining the check valve body 23 on the sliding valve body 22, a locking member 25 for preventing the sliding valve body 22 from being disengaged from the tubular body 21, a ventilation/feedwater button 26 secured to the upper end of tubular valve body 22 and projecting externally from the tubular body 21, a coiled compression spring 27 interposed between the button 26 and the locking member 25 for urging the sliding valve body 22 in a direction to project out of the tubular body 21, and O rings 28 interposed between the tubular body 21 and the sliding valve body 22 for preventing water leakage.

The bottomed tubular body 21 is in the form of a hollow cylinder having a bottom, and is provided with a flange-like mount 21a on its upper end, which may be secured to an outer wall 2a of the proximate operating end 2 by means of set screws 29. Adjacent to the upper end, the internal surface of the tubular body 21 is formed with threads 21b, which are engaged by threads 25a formed on the locking member 25, thus allowing the latter to be mounted thereon.

The sliding valve body 22 is in the form of a hollow cylinder having a reduced diameter in its upper portion. Intermediate its length, the valve body is formed with a circumferentially extending groove 31 in its outer periphery for communication with the feedwater path while toward its lower end, it has a circumferentially extending groove 32 in its outer periphery for communication with the ventilation path. The groove 32 communicates with a central bore 22d formed in the sliding valve body 22 through a ventilation passage 33. At its upper and lower ends, the internal surface of the sliding valve body 22 is formed with threads 22a and 22c, respectively. The threads 22a are threadably engaged by threads 26a formed on the ventilation/feedwater button 26, thereby allowing the latter to be mounted thereon. The threads 22c are threadably engaged by threads 24a formed on the check valve body retainer 24, thus allowing the latter to be mounted thereon.

The check valve body 23 includes a sleeve portion and a valve portion which are integrally molded and connected together by a thinner portion 23a and which are formed of a resilient material. In the region of the air delivery port 22b, the lower end of the sliding valve body 22 has a slightly greater diameter forming a shoulder, over which the check valve body is fitted. Retainer 24 is in the form of a bottomed, short sleeve having a ventilation hole 24b formed centrally in its bottom wall. When the threads 24a on the retainer 24 are engaged with the sliding valve body 22, the check valve body 23 is locked against withdrawal, over the air delivery port 22b.

The locking member 25 has a male thread member having a through-opening 25b formed centrally therein through which the upper end portion of the sliding valve body 22 having the reduced diameter extends. The lower portion of the locking member 25 has a reduced diameter and is formed with the threads 25a in its outer peripheral surface. The through-opening 25b has a slightly greater diameter toward its upper end, thus defining a step 25c centrally therein, against which the coiled spring 27 abuts. As will be seen, the spring 27 is disposed around the portion of the sliding valve body 22 having the reduced diameter and its other end bears against a flange 26b of the button 26. The lower portion of the button 26 is in the form of a hollow cylinder having the threads 26a formed in its outer periphery. The engagement between the threads 26a and the threads 22a on the valve body 22 permit the button to be mounted on the valve body 22, thus preventing the coiled spring 27 from being disengaged.

In operation, the sliding valve body 22 normally assumes its upper position under the resilience of the spring 27 when no external operation is applied. In this manner, the inlet side of the feedwater tube 8 is blocked while the inlet side of the ventilation tube 7 communicates with the groove 32. Consequently, the air flow from the air feeder (not shown) finds its way into the central bore 22d in the sliding valve body 22 through the groove 32 and the passage 33. Assuming that an air discharge port 26c which is formed at the upper end of the button 26 remains open, the flow resistance of the channel extending through the air discharge port 26c is less than the flow resistance of the channel extending through the valve body 23, ventilation hole 24b, and ventilation tube 7 to the distal end 4 of the endoscope 1, so that the air, upon entering the central bore 22d, is externally discharged through the air discharge port 26c.

When the air discharge port 26c is closed by a finger 17 as indicated in FIG. 4, the air flow to the exterior through the air discharge port 26c is interrupted, so that the internal pressure of the air within the central bore 22d increases as the air continues to be fed from the air feeder. Thereupon, the increased air pressure causes the valve portion of the check valve body 23 to be folded back about the thinner portion 23a, thus opening the air delivery port 22b. In this manner, the air is fed into the ventilation tube 7 through the port 22b and the ventilation hole 24b and from there is supplied to the distal end 4 of the endoscope 1.

As the sliding valve body 22 is pushed into the tubular body 21 while the air discharge port 26c is closed with the finger 17, the communication between the inlet side of the ventilation tube 7 and the groove 32 is interrupted while the inlet and the outlet side of the feedwater tube 8 communicate with each other through the groove 31. Hence, the air ceases to be fed through the ventilation tube 7 while the water is supplied to the distal end 4 of the endoscope 1 through the feedwater tube 8.

When the button 26 is released, the resilience of the spring 27 returns the sliding valve body 22 to its normal position where it projects the maximum distance from the tubular body 21. The inlet side of the feedwater tube 8 is again blocked to stop the supply of water while the inlet side of the ventilation tube 7 again communicates with the groove 32 to permit the air to be externally discharged through the air discharge port 26c. At this time, the switching apparatus 20 assumes its inoperative condition.

With the present ventilation/feedwater switching apparatus described above, if the check valve body 23 is damaged, it is only necessary that the locking member 25 which is threadably engaged with the tubular body 21 be removed from the latter in order for the sliding valve body 22 and the check valve body 23 mounted thereon to be removed from the tubular body 21. The retainer 24 can be dismounted from the sliding valve body 22 thus removed, thus permitting replacement or repair of the valve body 23 in a simple manner. After replacement or repair of the valve body 23, the sliding valve body 22 can be again inserted into the tubular body 21 and the locking member 25 mounted on the latter, whereupon the sliding valve body 22 is prevented from being withdrawn, enabling continued use of the switching apparatus 20.

Figure 5:
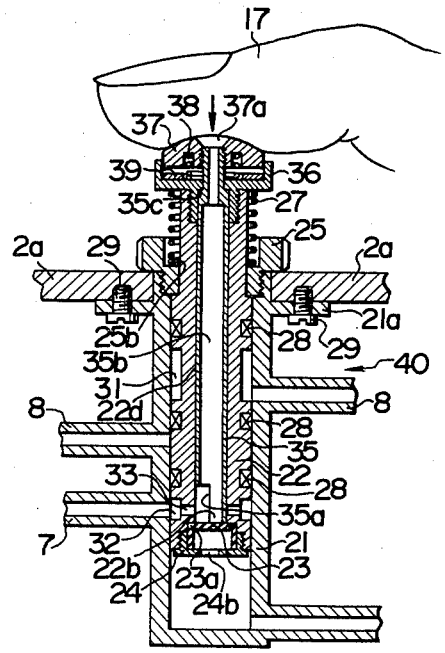
FIG. 5 is a longitudinal section of a ventilation/feedwater switching apparatus for endoscope according to another embodiment of the invention.

FIG. 5 shows a ventilation/feedwater switching apparatus 40 according to another embodiment of the invention in which a valve pushing rod 35 is assembled into the central bore 22b of the sliding valve body 22. The general arrangement is entirely similar to the switching apparatus 20 mentioned above in connection with FIG. 4 except the provision of the valve pushing rod 35 and the arrangement of the ventilation/feedwater button 36. Accordingly, corresponding parts are designated by like numerals as those used in FIG. 4, and will not be described.

The valve pushing rod 35 is in the form of a hollow body which is loosely fitted in the central bore 22d of the sliding valve body 22 so as to be movable in the vertical direction. The lower end of the rod 35 is located opposite to the upper surface of the check valve body 23. A notch 35a is formed in the rod 35 in a region where it is located opposite to the passage 33, thus allowing a communication between the passage 33 and a passage 35b extending through the rod 35. The rod 35 has an upper end of a reduced diameter which extends centrally through the button 36 to project above it, with a valve push button 37 fixedly mounted on the free end thereof.

The valve push button 37 is disposed so that its lower surface is located opposite to the upper surface of the button 36, with a coiled compression spring 38 being disposed between the two buttons 36, 37 to maintain the button 37 normally at an upper position where it is separated from the button 36 by a given distance. At this upper position of the valve push button 37, a step 35c formed adjacent to the upper end thereof between the portion of the reduced diameter and the remainder thereof bears against a corresponding step formed in a central opening which is formed in the ventilation/feedwater button 36. It will be noted that the top of the valve push button 37 is centrally formed with an opening 37a which provides a communication between the bore 35b and the atmosphere. An annular seal member 39 is applied to the upper surface of the button 36 so that when the valve push button 37 is depressed, the peripheral portion of the lower surface of the button 37 bears against the seal member 39 to provide a seal between the upper surface of the button 36 and the lower surface of the button 37.

With the switching apparatus 40 arranged as described above, in the event fluid within the coeliac cavity, blood or another contaminant flows backward through the ventilation tube 7 to the proximate operating end 2 to thereby cause the check valve body 23 to be fixed or to stick by coagulation, or in the event the valve body 23 is held tight against the air delivery port 22b as a result of non-use over a prolonged period of time, the valve push button 37 may be depressed against the resilience of the spring 38. In response thereto, the check valve body 23 is thrust downward by the lower end of the rod 35, whereby the check valve body 23 can be simply freed from its sticking relationship.

When the apparatus 40 is used to provide ventilation, the opening 37a of the button 37 may be blocked with a finger 17 as indicated in FIG. 5, whereupon the interruption of the external air flow through the throughopening 35b increases the internal air pressure within the bore 35b, which forces the check valve body 23 open to permit the air to be fed to the ventilation tube 7.

When a feedwater operation is desired, the button 37 may be depressed into abutment against button 36 while closing the opening 37a with the finger 17, followed by continued depression of buttons 36, 37 to move the sliding valve body 22 into the tubular body 21. As the sliding valve body 22 moves down, the communication between the inlet side of the ventilation tube 7 and the groove 32 is interrupted while the inlet side and the outlet side of the feedwater tube 8 communicate with each other through the groove 31, thus allowing the water to be fed into the distal end 4 of the endoscope 1 through the tube 8.

It is to be understood that during the water feed operation, the check valve body 23 is open and the opening 37a in the button 37 is blocked by the finger 17 and any clearance between the both buttons 36, 37 is closed by the seal member 39, so that any communication between the ventilation tube 7 and the feedwater tube 8 toward the distal end of the portion 3 cannot cause a backward flow of the water through the ventilation tube 7.

What is claimed is:

1. A ventilation and feedwater switching apparatus for an endoscope, said apparatus comprising:

a tubular body having an upper and a lower end and having an axis that extends from said upper to said lower end; and said tubular body being closed at said lower end; said tubular body having a feedwater inlet, a feedwater outlet, a ventilation inlet and a ventilation outlet formed therein; said tubular body being adapted to be disposed in the operating end of an endoscope in such a manner as to have said feedwater inlet and said ventilation inlet connected respectively to a feedwater supply line and to an air supply line of an endoscope in which said apparatus is disposed, and in such a manner as to have said feedwater outlet and said ventilation outlet connected respectively to a feedwater tube and a ventilation tube of the endoscope;

a sliding valve body having a central bore and received axially slidably, sealingly and removably in said tubular body; said sliding valve body having an upper and a lower end, its said lower end being received in said tubular body; said central bore communicating with the exterior of an endoscope in which said apparatus is disposed; and said sliding valve body having an air delivery port formed therein, said central bore communicating via said air delivery port with said ventilation outlet of said tubular body; said sliding valve body having a groove formed therein in such a manner as to permit said feedwater inlet and said feedwater outlet of said tubular body to communicate via said groove when said sliding valve body is in a first axial position in said tubular body; and said sliding valve body having a passage defined therein for permitting said ventilation inlet of said tubular body to communicate with said central bore when said sliding valve body is in a second axial position in said tubular body;

a check valve body detachably disposed at said lower end of said sliding valve body for closing said air delivery port in such a manner that if the communication of said central bore with the exterior of an endoscope in which said apparatus is disposed is blocked, the increasing internal air pressure in said central bore will force said check valve body to move to allow air to pass from said central bore to said ventilation outlet, thereby to allow the air to be fed into a coeliac cavity through the distal end of the endoscope; and a spring urging said sliding valve body to maintain it in said second axial position.

2. A ventilation and feedwater switching apparatus according to claim 1, further comprising a locking member having a through opening and being threadably engaged with said upper end of said tubular body, said upper end of said sliding valve body extending through said through opening and said sliding valve body being releasably retained in said tubular body by said locking member.

3. A ventilation and feedwater switching apparatus according to claim 1 further comprising means for removably securing the sliding valve body to the tubular body.

4. A ventilation and feedwater switching apparatus according to claim 1 or claim 3 wherein said groove is so shaped that when said sliding valve body is in said second axial position, said feedwter inlet does not communicate with said feedwater outlet.

5. A ventilation and feedwater switching apparatus according to claim 1 or claim 3, further comprising a valve push rod slidably disposed in said central bore of said sliding valve body and having an upper and lower end, said valve push rod having its lower end located opposite an upper surface of the check valve body for allowing said check valve body to be opened by a manual push operation.

6. A ventilation and feedwater switching apparatus according to claim 5, wherein said valve push rod is a hollow member having a notch adjacent to its said lower end, said notch permitting said passage to communicate with said central bore.

* * * * *